United States Patent
Viator et al.

(10) Patent No.: US 8,293,176 B2
(45) Date of Patent: Oct. 23, 2012

(54) PHOTO-ACOUSTIC DETECTION DEVICE AND METHOD

(75) Inventors: John A. Viator, Columbia, MO (US);
Paul S. Dale, Columbia, MO (US);
Ryan M. Weight, St. Joseph, MO (US);
Peter Sutovsky, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 13/110,624

(22) Filed: May 18, 2011

(65) Prior Publication Data
US 2011/0217762 A1    Sep. 8, 2011

Related U.S. Application Data

(62) Division of application No. 11/827,346, filed on Jul. 11, 2007, now Pat. No. 7,968,347.

(60) Provisional application No. 60/819,941, filed on Jul. 11, 2006.

(51) Int. Cl.
*G01N 21/01* (2006.01)
*G01N 21/05* (2006.01)

(52) U.S. Cl. ............ 422/82.09; 422/82.05; 422/82.13; 436/164; 435/29; 435/288.7; 73/861.18; 73/861.25; 73/861.26

(58) Field of Classification Search .......... 436/63, 436/64, 52, 164; 422/68.1, 82.05, 82.09, 422/82.13; 435/4, 29, 287.1, 288.7; 73/861.18, 73/861.25, 861.26; 356/73, 445
See application file for complete search history.

(56) References Cited

U.S. PATENT DOCUMENTS

| | | | |
|---|---|---|---|
| 5,125,749 A | 6/1992 | Leugers et al. | |
| 5,371,428 A * | 12/1994 | Kikuchi et al. | 310/324 |
| 5,720,894 A | 2/1998 | Neev et al. | |
| 5,781,294 A | 7/1998 | Nakata et al. | |
| 5,840,023 A | 11/1998 | Oraevsky et al. | |
| 5,941,821 A | 8/1999 | Chou | |
| 6,041,020 A | 3/2000 | Caron et al. | |
| 6,108,096 A | 8/2000 | Ushio et al. | |
| 7,039,446 B2 | 5/2006 | Ruchti et al. | |
| 7,322,972 B2 | 1/2008 | Viator et al. | |
| 7,390,628 B2 | 6/2008 | Batich | |
| 7,491,502 B2 | 2/2009 | Lin | |
| 7,968,347 B2 * | 6/2011 | Viator et al. | 436/164 |
| 2002/0026937 A1 | 3/2002 | Mault | |
| 2004/0039379 A1 | 2/2004 | Viator et al. | |

(Continued)

FOREIGN PATENT DOCUMENTS

WO    WO 2004/029593    4/2004

OTHER PUBLICATIONS

Laufer et al., "Pulsed near-infrared photoacoustic spectroscopy of blood," Proc. SPIE 5320, pp. 57-68, Jan. 2004.

(Continued)

*Primary Examiner* — Maureen Wallenhorst
(74) *Attorney, Agent, or Firm* — Greer, Burns & Crain Ltd.

(57) ABSTRACT

An example method for detecting an analyte in a sample of a bodily fluid includes the steps of exposing the bodily fluid sample to electromagnetic energy to cause a thermoelastic expansion in the analyte, and detecting a photoacoustic signal in the sample that results from the thermoelastic expansion.

20 Claims, 5 Drawing Sheets

U.S. PATENT DOCUMENTS

| | | |
|---|---|---|
| 2005/0134144 A1* | 6/2005 | Buhler et al. ............. 310/317 |
| 2005/0146726 A1* | 7/2005 | Balachandran et al. ...... 356/480 |
| 2005/0175540 A1 | 8/2005 | Oraevsky et al. |
| 2006/0264717 A1 | 11/2006 | Pesach et al. |
| 2009/0050568 A1 | 2/2009 | Fogelman et al. |

OTHER PUBLICATIONS

Paltauf, G. et al. "Measurement of laser-induced acoustic waves with a calibrated optical transducer." Journal of Applied Physics (Aug. 1997) 82 p. 1525-1531).

Karansci, T. et al. "Application of main component fraction collection method for purification of compound libraries," Journal of Chromatography A (Apr. 2005) 1079 p. 349-353.

Hejazi, Marjaneh et al. "A comparison of laser-ultrasound detection system sensitivity with a broad-band ultrasonic source for biomedical applications." Archives of Medical Research (Jul. 2005) 37 p. 322-327.

Yang, Sung-Yi et al., "A cell counting/sorting system incorporated with a microfabricated flow cytometer chip." Measuring Science and Technology (Jun. 2006) 17 p. 2001-2009.

Quimby, Richard S., et. al., "Photoacoustic effect in a flowing liquid", *Applied Optics*, (1987) 26, pp. 363-371.

Zhao, Zuomin, "Pulsed photoacoustic techniques and glucose determination in human blood and tissue", *Dissertation in the Department of Electrical Engineering and Infotech*, University of Oulu, 2002.

Office Action dated Jun. 2, 2010 from related U.S. Appl. No. 12/347,550.

Office Action dated Oct. 15, 2010 from related U.S. Appl. No. 12/347,550.

* cited by examiner

PHOTO-ACOUSTIC DETECTION DEVICE AND METHOD

REFERENCE TO RELATED APPLICATION AND PRIORITY CLAIM

The present application claims priority under 35 U.S.C. §120 and is a division of U.S. patent application Ser. No. 11/827,346, filed on Jul. 11, 2007, now U.S. Pat. No. 7,968,347 issued on Jun. 28, 2011, incorporated by reference herein, which claims priority under 35 U.S.C. §119 of U.S. Provisional Application Ser. No. 60/819,941, which was filed on Jul. 11, 2006.

FIELD OF THE INVENTION

A field of the invention is medical testing. One aspect of the invention concerns devices and method for the detection of analytes in a bodily fluid sample, with an example being circulating tumor cells in a blood sample.

BACKGROUND

Detection of analytes in bodily fluid samples is widely used for medicinal and other purposes. Applications include detection of pathogens, proteins, or other chemical compounds in blood, urine, bile, saliva, or other bodily fluids. Some example applications include drug screening, detection of disease, detection of a particular protein, and the like. By way of one particular example, detection of circulating tumor cells (CTCs) in human blood and lymph systems has the potential to aid clinical decision making in the treatment of cancer. The presence of CTCs may signify the onset of metastasis, indicate relapse, or may be used to monitor disease progression.

Present techniques and devices for the detection of CTCs have limits. Reverse Transcriptase Polymerase Chain Reaction (RT-PCR) is a technique that is used in practice. This technique involves the analysis of RNA. The technique takes significant time and involves a number of steps requiring the expertise of technicians to conduct assays. With the requirement of such expertise comes the potential for technician error. Freezing, culturing, assaying, etc. in the RT-PCR technique take both time and expertise. Results are also not immediately available to a treating physician.

Laser flow cytometry also has the potential to analyze samples for CTCs. However, CTC detection is evolving research area and optimal detection techniques are still a work-in-process. The technique, when and if it is perfected, however, remains one that shares some of the drawback to RT-PCR, e.g., skilled technician involvement and delays in obtaining and interpreting results.

Powerful diagnostic tools permit rapid and accurate evaluation. Critical to the treatment of cancer is the early stage detection of the onset of metastasis or relapse, and the monitoring of disease progression and the response of the disease to an ongoing course or treatment. Having accurate information about metastasis can provide a treating physician with the opportunity to be more effective and address the particular phase of the disease indicated by the metastasis. Accurately and rapidly detecting the presence of CTCs has the potential to advance the state of cancer diagnosis and treatment.

SUMMARY

An example system for detecting one or more analytes in a bodily fluid comprises a test chamber having at least one sidewall and configured to contain a bodily fluid test sample, an electromagnetic energy source configured to direct an energy source into said test chamber through said at least one sidewall and to induce a thermoelectric expansion in the one or more analytes, and a sensor configured to detect the thermoelastic expansion in the test sample. Preferably, the sensor is an acoustic sensor having a diaphragm that is deflected when an acoustic wave generated by said thermoelastic expansion strikes it and is arranged on the test chamber. In preferred embodiments, the sensor diaphragm is a piezoelectric diaphragm in fluid contact with the test sample. In preferred embodiments, the test chamber is transparent and wherein said electromagnetic energy source comprises a pulsed laser having a beam that illuminates an entire cross section of said test sample as it passes through said test chamber. In a preferred embodiment, the electromagnetic energy source is configured to direct an a first energy beam having a first wavelength but not a second wavelength, and at a different time to direct a second energy beam having the second wavelength but not the first wavelength into the test chamber so that the first energy beam induces a first thermoelastic expansion in a one or more analytes first analyte that absorbs the first wavelength but not the second wavelength, and the second beam induces a second thermoelastic expansion in a second analyte that absorbs the second wavelength but not the first wavelength. The first and second beams preferably extend across the entire cross sectional area of the flowing sample wherein no portion of the sample escapes illumination by the beam as it flows through the test chamber

DETAILED DESCRIPTION

Before example embodiments of the invention are discussed, it will be appreciated that the present invention includes methods as well as systems. For example, a method of the invention may include steps of using a system of the invention, and a system of the invention when used may be useful to carry out steps of a method of the invention. Accordingly, it will be appreciated that in describing a method of the invention description of a system may also be provided. Additionally, when describing a system of the invention description of a method of the invention may be made. For example, it will be appreciated that when describing details of a system of the invention description is simultaneously being provided of one or more methods of the invention, and vice versa.

The present invention is directed to methods and systems for detecting an analyte in a bodily fluid sample. As used herein, the term "analyte" is intended to be broadly interpreted as being a chemical, biological or other substance or material of interest. By way of example, an analyte may be a protein, a pathogen such as one or more cancer tumor cells, a chemical compound, or the like. Also, as used herein the term "bodily fluid" is intended to be broadly interpreted as meaning a liquid sample containing some fluid that originated in a body. Examples include bodily fluid samples contain blood, a blood plasma, urine, bile, saliva, semen, sperm, breast milk, cerebrospinal fluid, intracellular fluid, and the like. Importantly, as used herein the term "bodily fluid sample" is not limited to the fluid obtained from the body alone, but is also intended to include samples prepared using the fluid and a diluting fluid or carrier fluid. By way of example, a sample prepared by suspending a bodily fluid such as white blood cells in a saline solution is encompassed by the term "bodily fluid sample."

Figure 1:
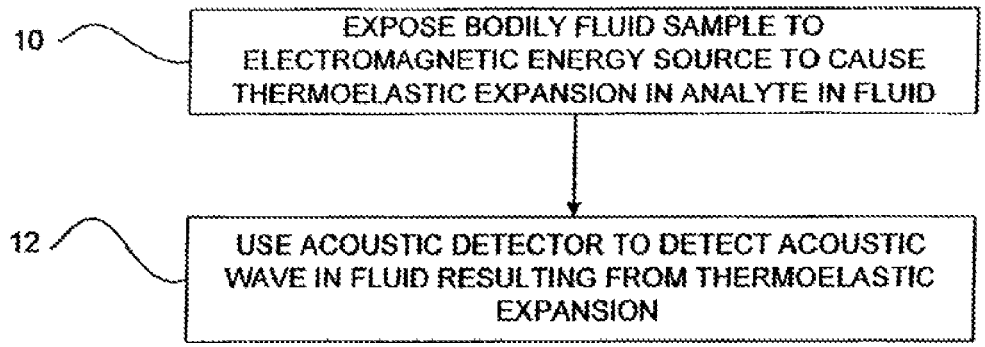
FIG. 1 is a flowchart illustrating one example method of the invention.

In order to best describe various example embodiments of the invention, description of general embodiments (and accordingly a general apparatus) is initially provided. FIG. 1 is a flowchart illustrating one example method of the invention. A bodily fluid sample is exposed to an electromagnetic energy source to cause a thermoelastic expansion in the analyte contained in the sample. Block 10. The bodily fluid sample may be any of the particular samples discussed above, including, for example, urine, blood or saliva. Also, it may be, for example, a test sample that includes one of these materials diluted, suspended, or other present together with a carrier fluid. A carrier fluid may be a solvent or a diluting fluid, with examples including aqueous solutions, saline solution, and the like.

The electromagnetic energy source may be any suitable energy source useful to cause a thermoelastic expansion. Examples include microwaves, visible and ultraviolet light, and the like. One example energy source is laser light. A thermoelastic expansion occurs when a material absorbs energy, is heated, and expands as a result. A photoacoustic signal results.

The method of FIG. 1 next includes a step of using an acoustic sensor to detect the acoustic signal that results from the thermoelastic expansion. Block 12. The photoacoustic signal may be a wave or other signal. Detection may include, for example, using a suitable detector to detect an acoustic wave that travels through the test sample. One example includes detecting the deflection of a diaphragm in fluid contact with the solution when the acoustic wave contacts a sensor diaphragm. Another is using an optical detector to measure a signal such as a perturbation (which may be a refraction change) in the sample following the thermoelastic expansion.

Figure 2:
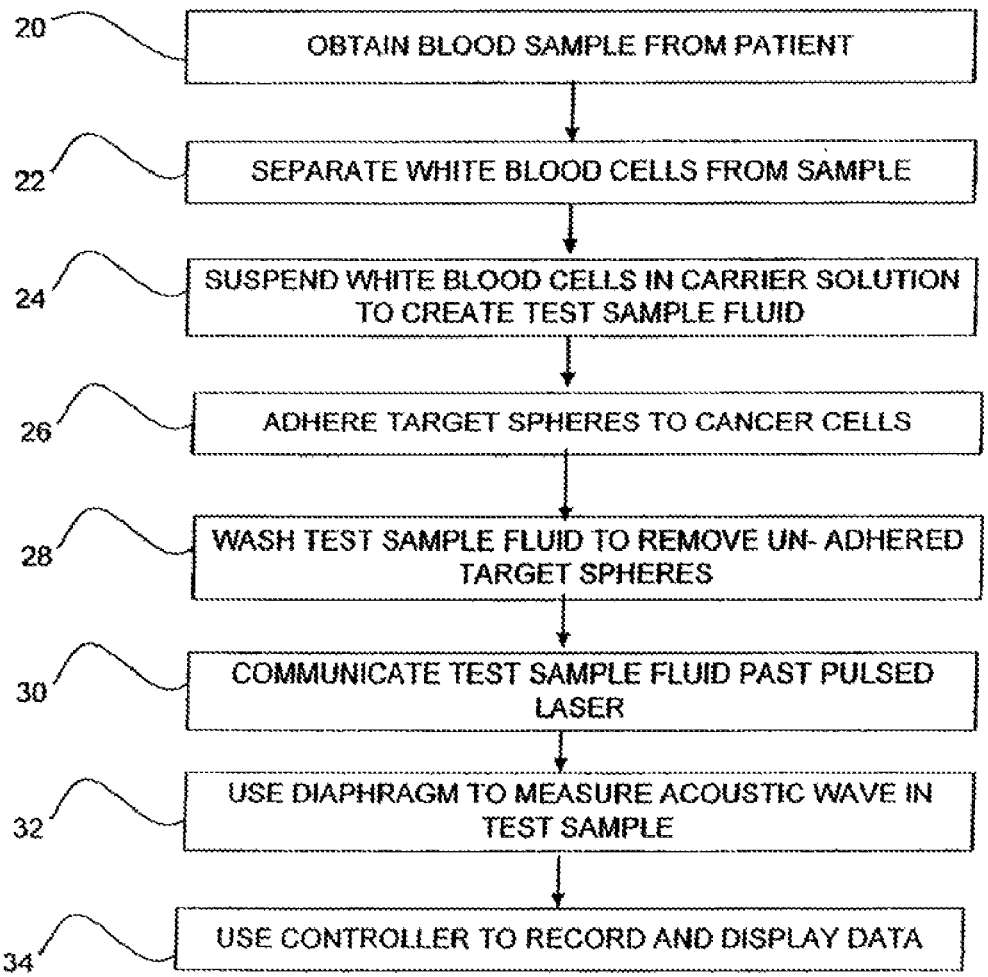
FIG. 2 is a flowchart illustrating a second example method of the invention.

By way of further example, FIG. 2 presents an additional example method of the invention. This example embodiment is directed to a method for detecting a pathogen, such as a cancer tumor cell, in a blood sample. The particular analyte application for this example embodiment could easily be changed, however.

In an initial step, a blood sample is obtained from a patient. Block 20. The sample may be, for example, as small in volume as a fraction of a milliliter to a quart or more. It may be obtained through a needle prick, of the skin, intravenously, or the like. The white blood cells are then separated from the blood sample. Block 22. This may be done, for example, using a centrifuge or other known separation method. The amount of white blood cells separated will depend, at least to an extent, on the size of the initial blood sample.

The thus separated white blood cells are then placed in a carrier fluid. This step may include, for example, suspension in a saline solution. Block 24. Suspension, as used herein, is intended to be broadly interpreted as meaning diluted with, carried with, placed in, or the like. Suspension of white cells in a carrier liquid, for example, may include diluting the cells in the liquid, mixing the cells into the liquid, or the like. The white blood cells may include one or more cancer tumor cells, such as melanin.

In an optional step of this example method, a plurality of target particles is adhered to the cancer cells. Block 26. The target particles or spheres can have a diameter of less than 0.01 millimeter. The particles may be, for example, microscale synthetic spheres selected for their ability to be detected by the electromagnetic energy that the sample will be exposed to. By way of particular example, gold nanoparticles, black latex spheres, dyes, quantum dots, or any other molecule that will give the cell some color (such as biotin) may be used that are good absorbers of electromagnetic energy such as a laser light.

The target particles may be treated to cause them to be attracted to and adhere to the cancer cell. Treatment may include providing surface anti-bodies known to be attracted to the analyte of interest, electrical charging, or the like. In one example step, the targets are attached by creating a bond via an antibody-receptor pair. This provides the specificity and strength necessary for the attachment. The target particle is functionalized to attach to the specific antibody. These functionalized particles are introduced to the sample containing the cells with the paired receptors. After washing away excess spheres that didn't attach to a cancer cell receptor, cancer cells have spheres attached to their receptors (usually surface receptors, though not necessarily).

This optional step can be useful to "amplify" the detection threshold of the one or more cancer cells. An alternative step includes dyeing the analyte with a suitable absorbing coloration. Excess target particles (that are not adhered to the cancer cells) can be removed from the test sample through washing or other known methods. Block 28.

The test sample is then communicated past a pulsed laser light. Block 30. This step may include, for example, placing the sample in a system of the invention that includes a reservoir, a flow generator such as a pump, and a conduit connecting the reservoir to a test chamber where the laser light is directed. When the cancer cell of interest is melanoma, for example, the laser light used to interrogate the fluid sample can be anywhere in the visible range, and in other wavelengths that melanin absorbs. When the cancer cell is other than melanoma, detection will be achieved through absorption by the target spheres.

Also, methods and systems of the invention may include steps and elements for using different wavelengths of light to detect particular analytes. If one analyte is known to absorb light of wavelength X and not Y, for example, a test sample can be interrogated with both X and Y wavelength light. If a positive signal results when interrogated with X but not Y, an indication that the particular analyte is present is provided.

The pulsed laser light is absorbed by the melanin and induces a thermoelastic expansion in it, which results in an acoustic wave in the solution. The acoustic wave is measured using a detector such as a diaphragm. Block 32. The magnitude of deflection of the diaphragm may indicate, for example, not only the presence of a cancer cell but further an indication of its size, density, coloration, concentration, and other properties. Data from the diaphragm is recorded and displayed using a controller. Block 34. This step may include, for example, amplifying an electrical signal from the diaphragm, recording it in a memory, and displaying it on a display.

Having now described some general example methods of the invention, more detailed description of other methods, systems and details of invention embodiments can be provided. In order to do so, some discussion of photoacoustics as it relates to some invention embodiments will be helpful.

Photoacoustics, also referred to as laser-induced ultrasound, uses short duration pulsed light to create ultrasonic acoustic waves in an optically absorbing medium. These acoustic waves are generated based upon the thermoelastic properties of targeted analytes, which in many invention embodiment (but not all) will comprise chromophores. Chromophores by definition are atoms or molecules within a compound that are responsible for the color of the given compound. Inherently, they present color by partially absorbing wavelengths composing the visible spectrum of incident light. The non-absorbing wavelengths are subject to scattering and reflectance as determined by the composition of the particular chromophore, thus emitting the color representative of the reflected wavelengths. Photoacoustics is based upon the absorbed portion of incident light. As light is absorbed by irradiated chromophores, the optical energy gets converted into kinetic thermal energy trapped within the chromophore and subsequent thermal expansion of the atoms ensues. Thermoelastic expansion occurs when the condition of stress confinement is achieved by depositing direct energy unto a chromophore in a continuous manner such that energy is unable to propagate away except by means of eventual convection with surrounding mediums. This condition is expressed as:

$$t_p < \delta/c_s$$

where $t_p$ is the laser pulse duration, $\delta$ is the absorption depth of laser energy, and $C_s$ is the speed of sound in the medium. It is assumed that the absorption depth, $\delta$ is smaller than the diameter of the laser beam.

Transient thermoelastic expansion can be achieved by irradiating with short pulses of concentrated laser light allowing for elastic expansion and contraction of an absorbing molecule. This thermoelastic expansion and subsequent contraction results in the production of longitudinal ultrasonic waves propagating in all directions away from the thermally excited medium of interest. Stronger heat generation will produce a stronger acoustic wave via greater thermoelastic expansion. Therefore, a strong optical absorber emanates a strong acoustic wave. Conceptually, photoacoustics can be described as pulsed laser energy quickly absorbed by a scattering medium such that transient thermoelastic expansion results in formation and propagation of acoustic energy. Thermoelastic expansion, as used in photoacoustics, can be described by (assuming a pure absorber where $\delta = 1/\mu_0$)

$$p(z) = \frac{1}{2}\mu_a \Gamma e^{\mu_a z}$$

where p(z) represents pressure at depth z, $\mu_a$ is the optical absorption coefficient of the tissue, $\Gamma$ is the Gruneisen coefficient, which denotes the fraction of optical energy which is converted to acoustic energy. It is temperature dependent and is equal to 0.12 at room temperature for most tissue.

The total photoacoustic energy resultant from the absorption of a beam is directly related to chromophore content. The amount of thermoelastic expansion as given in the above equation is directly related to the absorption coefficient $\mu_a$ of the chromophore. The absorption coefficient is derived from the molar extinction coefficient and chromophore concentration as described by: $\mu_a = 2.3 \epsilon c$ where c is the concentration of specific chromophore and $\epsilon$ is the molar extinction coefficient of the compound. These relationships are useful to characterize the chromophore above and beyond its detection. For example, the magnitude of the photoacoustic energy detected can be useful to estimate the size, density, and identity of an unknown chromophore.

Acoustic pressure is proportional to energy per unit volume given as Joules per $cm^3$. If a spot size is held constant, the integral of pressure over depth yields the total absorbed energy as given by:

$$E_a = \int_0 P_o(z) dz$$

$E_\alpha$ is the total absorbed energy by the chromophore and $P_o(z)$ is the initial pressure as a function of depth z. The integral gives a quantity expressed in terms of $J/cm^2$, so the total energy detected is related to this quantity by the detector active area. The amount of energy ($E_a$) absorbed is directly related to the amount of incident light energy upon the medium (also given as $J/cm^2$) to a certain limit determined by the absorption capacity of the specific chromophore.

Detection of these minute photoacoustic waves is equally as important as their production in many invention embodiments. Photoacoustic detection methods can vary drastically from one experimental design to another. One element discovered to be useful in methods and apparatuses of the invention is a piezoelectric copolymer in electrical connection with two electrodes, one being the ground wire and the other measuring the positive voltage change of the film. These films may be constructed of polyvinylidene difluoride, or PVDF, and may or may not incorporate an aluminum coating that acts as a conducting element. Many other detector configurations are contemplated, however, including (by way of example and not limitation) other diaphragms whose deflection may be measured when an acoustic wave strikes it, optical detectors that detect a change in reflective and/or refractive index in a fluid as an acoustic wave travels therein, and the like.

As longitudinal acoustic waves propagate towards the piezoelectric film of one example system and method, pressure accumulates according to the magnitude of each pressure wave. As these pressure waves come into contact with the piezoelectric film, the lateral surface of the film impacted by the pressure wave shifts, disrupting the entropically stabilized bilayer. The disruption of the polymer layer causes an electrical charge to form between the two copolymer layers that can be detected by two conducting electrodes as a voltage spike. Using information on the magnitude of the signal (e.g., the amplitude of the voltage spike) and/or the time difference between sending a laser pulse and receiving the pressure wave, chromophore density and concentration can be quantified as well as relative location to that of the PVDF film as described in detail below. Some systems and methods of the invention include elements and steps of taking these measurements and using the resultant data to measure density and the like.

As discussed above, some examples of the present invention include apparatuses and methods for detecting the presence of melanotic cancer cells within the human hematogenic system. Some systems and methods employ photoacoustic technology as an in vitro method of screening and quantifying disseminating tumor cells for the purpose of cancer detection or as a method for determining the effectiveness of chemotherapeutics. Such devices and methods offer a way of improving upon standard detection protocols while alleviating many of the problematic symptoms of alternative detection methods of the prior art.

Some photoacoustic detection systems and methods of the invention provide benefits and advantages including the ability to accurately pinpoint both early and late stage disseminated cancerous cells present within the bloodstream. This provides a relatively pain-free and lower cost alternative to clinical protocols of surgically based detection methods as well as over a much needed mechanism for the early detection of disease. It is proposed that this detection system may provide a method for precise and unprecedented detection thresholds by identifying single melanoma cells in the presence of millions of secondary blood constituent cells.

One example detection device provides a flow system through which solutions of interest may be introduced for the purpose of exciting as few as a single melanotic cancer cell by pulsed laser excitation. In order to do so, a transparent flow cell, or excitation chamber, conducive to laser excitation is incorporated into the system. A reliable acoustic detection system or similar detection element is also included to capture photoacoustic waves. A signal element is used to convert acoustic waves produced by melanotic excitation to voltage signals that can be displayed for analysis.

Figure 3:
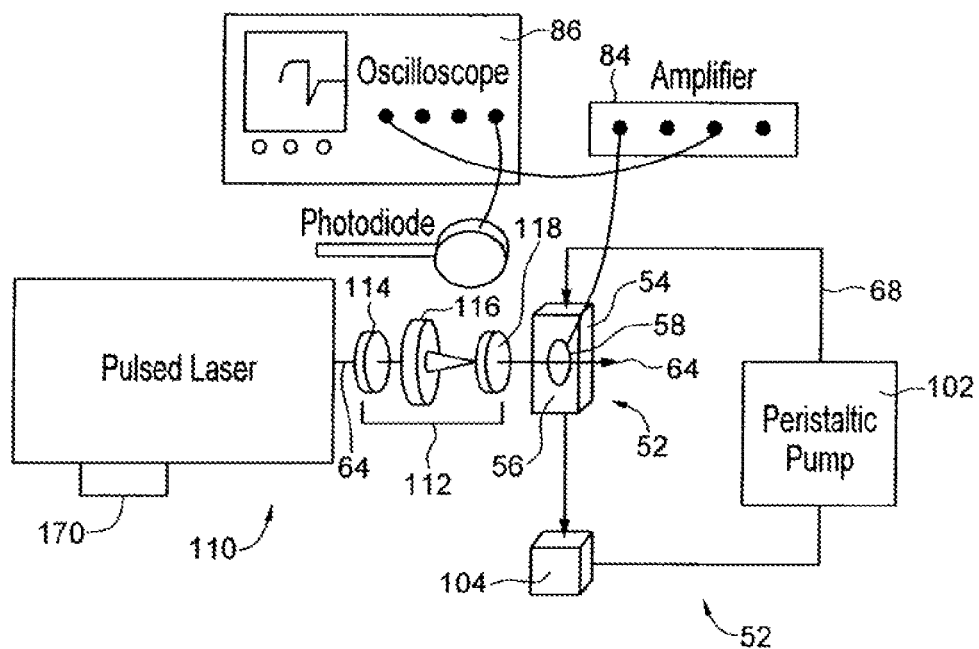
FIG. 3 is a schematic illustration of an example system of the invention and is also useful to illustrate an example method of the invention.

An example detection system 50 of the invention is schematically shown in FIG. 3. It includes, among other elements, an excitation chamber or flow cell 52. The flow cell 52 is the chamber where laser excitation and acoustic wave propagation and detection occurs. A number of different flow cells are suitable for use in methods and systems of the invention. Some include transparent sidewalls that allow an electromagnetic energy source, with an example being a laser, to be located external to the cell. One example cell 52 found to be useful is a customized flow cell commercially available from Spectrocell, Oreland, Pa.). The cell 52 is shown schematically in FIG. 3, and is illustrated in greater detail in FIG. 4.

Figure 4A:
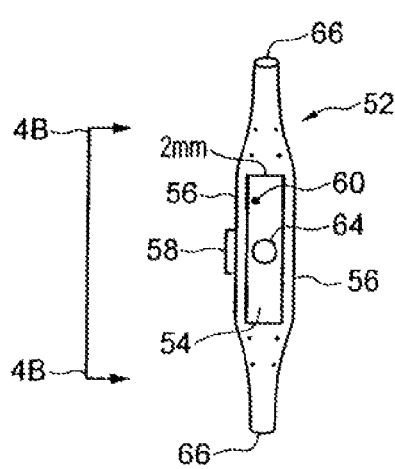
FIG. 4 illustrates the test cell of the system of FIG. 3, with FIG. 4(B) illustrating the cell when viewed along the line 4B-4B of FIG. 4(A) in the direction shown.
Figure 4B:
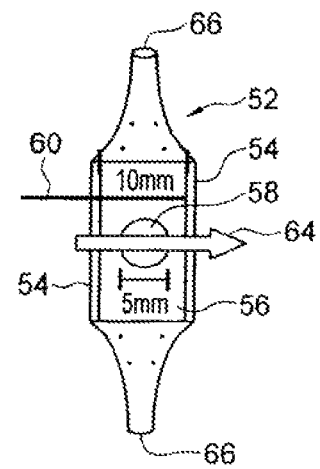

FIGS. 4(A) and 4(B) show the flow cell 52. It has a generally rectangular box three dimensional shape, including opposing first and second narrow sidewalls 54 joined to wider opposing sidewalls 56. Dimensions shown are illustrative only, other dimensions will be useful. As shown by FIG. 4B, in the example cell 52 the narrow sidewalls have a width of about 2 mm (along the width of FIG. FIG. 4B) and the wider sidewalls have a width of about 10 mm. The cell 52 also includes a detection diaphragm 58 arranged on one of the wider sidewalls 56 and covering a cylindrical passage of about the same diameter in the sidewall 56 whereby it is in fluid contact with the test sample in the cell 52 interior. In the example cell 52, the diaphragm 58 is a 5 mm diameter PVDF film. The cell 52 also includes a positive electrode 60 extending out from the cell interior and through a small passage in one of the narrow sidewalls 54 and in fluid contact with the test sample therein.

FIG. 4(B) is a schematic showing dimensions of the example flow cell 52 and an incident laser beam 64 direction as it passes through the cell 52 from an external source. The example flow cell 52 has dimensions of about 2×10×45 mm (walls 54 width×wall 56 width×height) for a total fluidic volume of about 0.9 ml. Other dimensions are contemplated and will be useful. Particular dimensions will be selected based on design considerations including energy beam size, desired test sample volumetric throughput, flow rate, and the like.

The top and bottom of the flow chamber 52 are tapered to cylindrical ports 66 with an inner diameter of about 2.7 mm and an outer diameter of about 4.95 mm. These ports 66 serve to connect the cell to the conduit 68 (FIG. 3) that communicates the test sample fluid into and out of the cell 52.

The high intensity laser beam 64 is directed into one of the narrow sidewalls 54 of the flow cell 2, opposite that of the detection diaphragm 58, at a height approximately equal to that of the detection aperture 54. The laser beam 64 passes through the fluid test sample in the cell 52 interior and out through the opposing narrow sidewall 54.

As discussed above, the laser beam is configured to induce a thermoelastic reaction in the test sample which results in an acoustic wave. In some methods and apparatuses of the invention, the acoustic wave is detected through use of a diaphragm 58 that deflects when the acoustic wave contacts it. The example diaphragm 58 are in fluid contact with the test sample. Deflection of the diaphragm 58 may be detected through any of several methods. In the example flow cell 52, the piezoelectric film diaphragm 58 on the wider cell sidewall 56 is employed as an acoustic wave sensor diaphragm.

Figure 5:
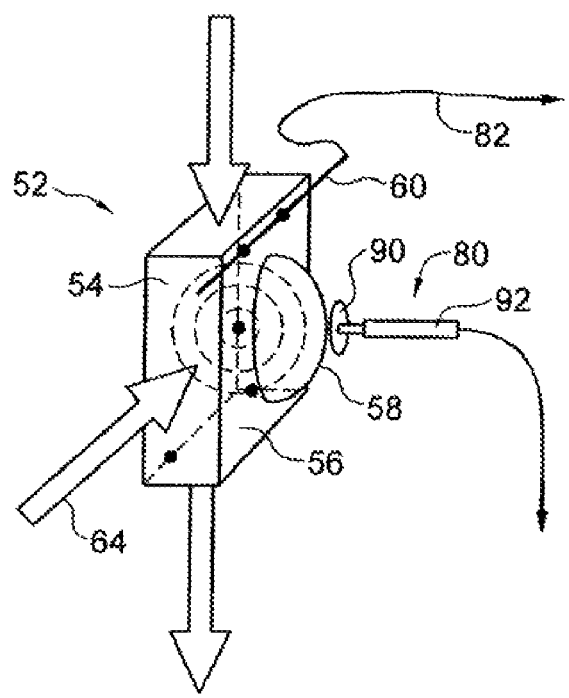
FIG. 5 illustrates the test cell of the system of FIG. 3.

As is best illustrated by the schematic of FIG. 5, the diaphragm 58 is arranged about a pair of electrodes including the internal electrode 60 and an external electrode shown generally at 80 which will be described below. This configuration results in an electric field between the electrodes 60 and 80 to be disturbed and fluctuate when the diaphragm 58 is deflected therebetween. As will be discussed in detail herein below, the electric field fluctuation can be measured and used to signal the presence of an acoustic wave, and therefore an analyte. The amount of deflection of the diaphragm can be used to estimate qualities of the detected analyte, including for example its coloration, density, mass and/or size.

The diaphragm or piezoelectric film 58 in the example system 50 is cut to a diameter slightly larger than a 5 mm diameter passage on one of the wider (10 mm) sidewalls 56 and is affixed to the outside of the flow cell 52 by a 100% silicone sealant available from DAP Inc., Baltimore, Md. The piezoelectric film 54 is a 100 micron polyvinylidene difluoride (PVDF) copolymer film available from Ktech Corp., Albuquerque, N. Mex.

Although many other configurations are contemplated, copper electrodes are used for both positive signal detection and grounding. Different mechanisms were used for each. The example positive electrode 60 is a stripped 0.6 mm diameter copper wire approximately 17 mm in length inserted into the narrow (2 mm wide) sidewall 54 of the flow cell 52 as shown in FIGS. 4A-B and FIG. 5. The electrode 60 is sealed with 100% silicon sealant. It extends over much of the horizontal 10 mm width of the wider sidewall 56 and leaves an external end which is connected by a conductor such as wire 82 for transfer to a controller, which may include one or more of a computer, an amplifier 84 (FIG. 3), oscilloscope 86 (FIG. 3), or the like.

The negative electrode 80, or ground, consists of a thin, circular 4 mm diameter copper plate 90 from Small Parts, Inc., Miami Lakes, Fla., soldered to a short length of 3.5 mm diameter wire which is in turn soldered to a 31-221-VP BNC connector 92 from Jameco Electronics, Belmont, Calif. which connects to a grounded RG 58 coaxial cable 94 from Pomona Electronics, Everett, Wash. The flat copper plate 90 is flush against the external side of the PVDF film 54. This provides a ground to one side of the piezoelectric film.

Referring once again to the schematic of FIG. 3, experimental test sample solutions are pumped through the circulation conduit 68 using a pump 102. In the example system 50, the pump 102 is a peristaltic pump, namely a Masterflex L/S Economy Drive.

It is noted that although many systems and methods of the invention include circulation of test samples, others do not.

Circulation is beneficial in many applications, however, since it allows for a relatively large sample to be subjected to a small, compact energy beam as it is circulated past the beam.

The circulation conduit 68 in the example system comprises L/S 14 platinum-cured silicon tubing available from Cole-Parmer Instruments, Vernon Hills, Ill. Although other pumps can be used, a peristaltic pump offers advantages in that no mechanical pump elements directly interact with the fluid sample in the conduit 100. In the example system 50, about 15 ml of test sample solutions are entered into a 13.75 $cm^3$ open reservoir 104. The peristaltic pump 102 provides negative pressure, circulating test sample fluid out of the reservoir 102, urging it through the test cell 52, and finally returning it to the reservoir 104 through an open top. The silicon tubing 68 is size fitted to the output and input ports 66 (FIG. 4) of the flow cell 52. In the example system 50, test sample solutions circulate at a speed averaging about 9 ml/minute, allowing for analytes of interest to be excited 235 times when vertically crossing the beam path 64 (FIG. 4) of a 5 ns pulsed laser with a 1 mm spot size (average conditions for a given setup).

Those knowledgeable in the art will appreciate that a variety of different electromagnetic energy sources will be useful with methods and apparatuses of the invention. Lasers, and particularly pulsed laser light, are one example believed to be useful. A wide variety of lasers are suitable for use in different methods and systems of the invention. Factors such as light wavelength, beam width, intensity, and the like can be specified as desired for a particular application.

In the example system 50, photoacoustic excitation is made possible by a sharply focused pulsed laser system shown generally at 110 in FIG. 3. Although a variety of different lasers and other electromagnetic energy sources can be used, the laser system 110 in the example system 50 includes a Q-switched, frequency tripled Neodymium-doped Yttrium Aluminum Garnet or Nd:YAG laser from Quantel Les Ulis, Cedex, France housed in a Vibrant Integrated Tunable Laser System from Opotek, Carlsbad, Calif. The Nd:YAG is a pumped laser that emits 1024 nm pulsed laser light by an optical switch dubbed the "Q-switch" which acts as a gate to release light at the maximum neodymium ion inversion. Once released, laser light is reflected by two mirrors within the Vibrant into a second harmonic generator where the wavelength is converted to 532 nm then into a third harmonic generator where it is converted to 355 nm. The 355 nm laser light is pumped into an Optical Parametric Oscillator or OPO.

The OPO contains a Beta Barium Borate crystal that tunes by the electronically controlled rotating of the crystal with respect to beam. The OPO converts the 355 nm input wavelength into two beams, the signal and the idler, each having longer wavelengths than the input beam. A cavity termed the Double Resonating Oscillator oscillates both the idler and the signal wavelengths while the tuning angle of the crystal determines a phase match that produces the desired wavelength which is then released from the cavity. The tuning angle is controlled by a stepping motor operated by an external, computer generated program.

The OPO allows for the output of variable wavelengths ranging from 410 nm to 710 nm. The particular wavelength of light utilized in methods and systems of the invention using a laser will depend on applications including the wavelength that will be absorbed by the analyte being searched for, and the like. By way of example, laser light of about 450 nm can be useful.

Following the OPO, the beam passes through a polarizer. In some systems of the invention, the laser light is then coupled by a lens into a fiber optics fiber carrier (with an example being a 1.5 mm standard silica fiber) for light transfer. While this can be useful, in some applications the fiber can be subject to breaks and loss of energy resulting in poor results. Other example devices and methods, including the example system 50 utilizes an "open" delivery system, wherein laser light travels through the atmosphere from the laser system 110 to the test cell 52. In the example system 50, use of open light increased energy input into the test cell 52 from a range of 7.0-8.0 mJ output when using fiber to 11-12 mJ.

In some example systems and methods of the invention, a tradeoff can exist between radiant energy strength and sufficient radiant exposure. That is, a radiant beam is desirably large enough to encompass all the analyte or chromophores that may pass through the detection cell 52 but not be too large such that it will not provide enough energy for proficient signal strength. This tradeoff must further be balanced against costs of a laser system 110—while conceivably a large enough system could be obtained to provide an extremely large diameter beam of extremely large energy, costs for doing so may be prohibitive.

The laser beam 64 exiting the output port of the example Vibrant laser system 110 takes the form of an ellipse. In such example methods and systems, the beam should be focused into the flow cell 52 so that the beam profile takes on a circular shape ranging between about 1 mm and 2 mm in diameter so as to cleanly enter the 2 mm wall of the flow cell 52. Different size beams will be useful for different size cells, but generally it is advantageous to configure the beam to have a diameter that extends across the entire width of the cell 52. This allows for the entire cross section of the circulating test sample to be irradiated by the beam. Further, configuring the test cell in a geometry such as that shown in FIG. 4 wherein the rectangular box shaped cell has a thin side (e.g., the 2 mm side) and a wider side (e.g., the 10 mm side) can be advantageous. In such geometries, the beam 64 can pass through opposing narrow sidewalls 54 and irradiate the entire cross section of the circulating sample within the test cell 52.

Referring again to the schematic of FIG. 1, in the example system 50 the output beam 64 was spatially oriented by a series of lens shown generally at 112. These include a cylindrical lens 114 (lens no. LJ1014L2-B, from Thorlabs, Newton, N.J.) in addition to two collimating plano-convex lenses, 100 mm (element 116) and 50 mm focal length (element 118) (lens nos. LA1509 and LA1131, also from Thorlabs, Newton, N.J.) before entering the flow cell 52. The result was the beam 64 having a 1 to 2 mm diameter cylindrical spot size measuring between 11.0-12.0 mJ when it enters the cell 52. Spot size was determined by irradiating ZP-IT Laser Alignment Paper from Kentek Corp., Pittsfield, N.H., with a single 5 ns pulse and measuring the diameter of the burn.

Figure 6:
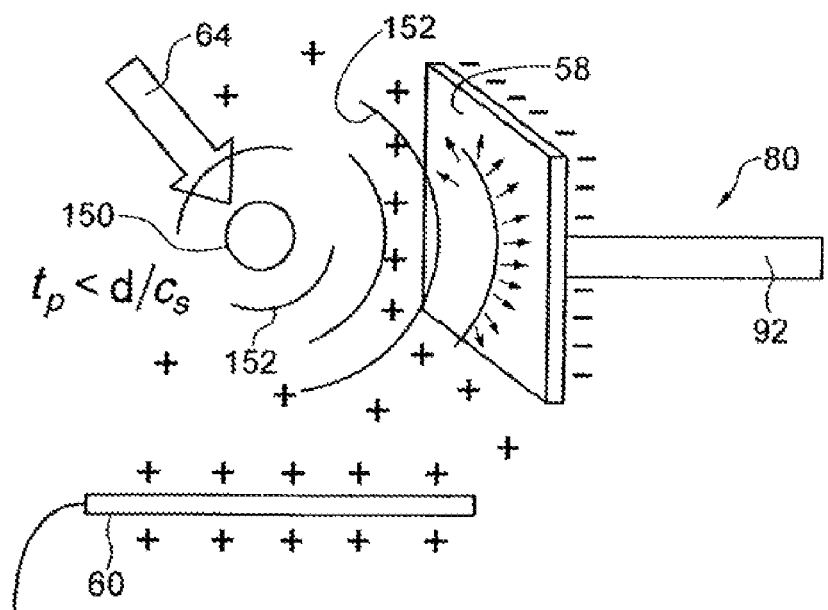
FIG. 6 schematically illustrates detection of a thermoelastic event using the sensor of the system of FIG. 3.

In order to more fully illustrate the excitation and detection mechanisms of some systems and methods of the invention, the schematic of FIG. 6 is presented. The photoacoustic mechanism as it pertains to some example methods and systems of the invention begins with the excitation of an analyte or chromophore 150, in this example case melanoma or its related tissue phantom. In the example system 50 and related example methods, laser light 54 is pulsed at a rate of about 5 ns and is at a wavelength of about 450 nm. The frequency of the pulses may be selected as desired depending on factors such as cell geometry and scale, sample flow rate, analyte being searched for, and the like. In many example systems and methods, frequencies of faster than a millisecond are believed useful, faster than a microsecond, and in many applications (such as the example system 50) on the order of nanosecond (ns).

This bombards the chromophore 150 of interest in the test sample as it passes through the beam 64. The chromophore 150 absorbs at least a portion of the incident light from the beam 64 and photon energy is transformed into thermal energy. The increase in thermal energy causes a temperature rise within the chromophore 150 and a kinetic thermo-elastic expansion ensues. The thermo-elastic expansion is transient due to the pulsed nature of the incident laser light 64. Since the excitation pulses are short enough in duration that no thermal heat escapes the chromophore 150, small elastic enlargements of the cells 150 occur within the solution in a manner such that pressure waves 152 are propagated away from the source in the range of 1-50 MHz.

Longitudinal pressure waves, such as those emanated from a photoacoustic source, propagate parallel to the direction of the wave. The resulting effect is that of a compression wave or moving band of high pressure. This high pressure band moves freely in solution (such as the test sample environment within the flow cell 52) away from the source in all directions. The speed of the wave varies with application, and may be for example, at about 5 mm per second. A portion of these waves 152 come into contact with the diaphragm 58 and strike it as a mallet would strike the surface of a drum.

The PVDF film 58 is a highly ordered copolymer that can be likened to a lipid bilayer in a biological system. At steady state, or ground, conditions are entropically favorable for an ordered copolymer structure. When an acoustic wave 152 strikes a surface of the film 58, that copolymer layer is disrupted, increasing the entropy of the system and consequently forming a charge on the disrupted surface. The exterior of the film 58 is grounded by the copper plate electrode 90 (FIG. 5) therefore conferring a positive charge to the interior surface of the PVDF film 58.

In other example embodiments, the PVDF film or other sensor may be decreased in size which may increase signal strength by decreasing the surface area of the detector and eliminate some signal dampening. Chemicals such as Indium Tin Oxide may be applied to the positive surface of the PVDF to increase conductance at the surface of the film.

The positive voltage produced by the photoacoustic phenomenon is conducted throughout the interior of the test cell 52 by a conductive carrier solution such as the 1.8% saline solution which is used in some example methods and systems of the invention. The electrode 60 described above carries the charge out of the flow cell 52 for further analysis.

In the example system 50, the resulting electrical signal is amplified for ease of detection. The transduced voltage of a photoacoustic effect is carried to amplifier 84 (FIG. 3) which is in the example system is a SR445A 350 MHz Amplifier from Stanford Research Systems, Sunnyvale, Calif. where it is amplified by four stages each providing a gain of 5 for an amplification range of 5 to 125. In the example system 50, voltage signals are displayed by the oscilloscope 86, which in the example system 50 is a TDS 2024 200 Mhz Oscilloscope from Tektronix, Beaverton, Oreg., triggered by a photodiode available from Thorlabs, Newton, N.J., upon each laser firing.

It is noted that the amplifier 84 and oscilloscope 86 are one example of electronics useful to receive and analyze signals from the test cell 52. In other example systems, these components are replaced by a single controller, which may be, for example, a processor based device with internal components useful to amplify and process the voltage signal from the cell 52. Such a controller may output data including visual and/or audio data indicating presence of an acoustic wave and therefore a chromophore of interest. The controller may also record data in a memory, and record other data such as time, test sample identification and the like. The controller may be, for example, a computer.

As noted above, FIGS. 3-6 are schematic only, and have been provided to illustrate various elements of one example embodiment of a system and method of the invention. Other systems and methods will vary from those illustrated above. The system as illustrated, in fact, represents an experimental apparatus as may be configured in a laboratory, for example. Commercial embodiments of systems and methods of the invention may be configured using alternate conduits, cells, reservoirs, and the like.

By way of example, some commercial embodiments may be configured in a housing, using a computer controller that is linked to the laser, pump, and that provides data acquisition, recording, processing and display. Some embodiments of the invention may value portability and be configured as such. Other variations will be apparent to those knowledgeable in the art.

By way of example, an additional system of the invention was configured using an alternate cell configuration. The cell was configured as a dual chamber device constructed from standard microscope slides available from Fisher Scientific, Pittsburgh, Pa., cyanoacrylate from Loctite, Avon, Ohio, 100% silicone sealant from Dow Corning, Baltimore, Md., and Nylon sheet plastic from Small Parts Inc., Miami Lakes, Fla. These materials were carefully cut and constructed by hand and sometimes resulted in results that were less reliable than those obtained using the example system 50. One chamber served as the flow chamber and conducted a positive signal, similar to the flow cell 52 of FIGS. 3-4. The second chamber was a stagnant reservoir tilled with saline solution that was grounded by an electrode inserted into the chamber.

Separating the two chambers was a glass divider with a 5 mm diameter passage cut into it. The PVDF film was sealed onto the face of the divider on the grounded side. Consequently, this mechanism functioned in the same manner as the diaphragm in the example system 50 and was used to realize the idea that a proposed photoacoustic device. It was essentially consistent with the cell 52 discussed above, except that the second saline filled chamber replaced the grounded electrode 80.

Other variations of the cell 52 have likewise been utilized. By way of one example, in an alternate configuration the internal electrode 60 was eliminated. This configuration utilized an additional positive, copper plate electrode housed on the opposite side of ground electrode 80 that clamped both sides of an aluminum plated PVDF film together. This film replaced the diaphragm 58 shown above. The aluminum plating can serve as conductors for both the positive and ground signals, avoiding the use of the invasive electrode 60 into the flow cell.

It was discovered, however, that the aluminum plating to some degree compromised the structural integrity of the PVDF film 58 and resulted in poor signal strength. It is believed the lack of signal strength may have been a result of signal shorting by electrode contact. To address this issue the example system 50 shown above utilizes the non-plated film 58, internal positive electrode 60, and direct grounding by an external plated electrode 80 placed directly on the detection area of the PVDF film 58. Although the configuration shown above proved beneficial over the plated film configuration in some applications, this alternate electrode configuration may be useful in some applications.

Other variations and modifications of the system and method as shown above arc also contemplated. Some modifications, for example, will be useful to adjust the threshold of detection of systems and methods of the invention. This can be adjusted, at least to a degree, through adjustment of signal strength. Increased signal strength will generally result in increased sensitivity. Increases in signal strength, however, must be balanced against resultant signal noise. A high signal to noise ratio is desirable. Those knowledgeable in the art will appreciate that tuning of a system to achieve this will be possible and may vary on particular application details. Some example system and method elements that can be varied to affect signal strength and noise ratio are discussed below.

For example, an improvement in signal strength in the example system 50 was achieved due to an increase in detection aperture size in the sidewall 56 underlying the diaphragm 58 from about 2 mm to about 5 mm in diameter. Generally, larger detection apertures increase the likelihood that acoustic wave collection will occur from the surrounding medium. An additional improvement in signal strength was achieved though using a relatively small overall cell volume, and particularly in regards to the narrow 2 mm side wall 54 width. This narrow 2 mm sidewall 54 width constrains the chromophores passing through the flow cell and forces the entire medium to pass through the excitation beam path assuring that no chromophore passing through the cell is missed.

Although the 2 mm value is only one example of a useful size, many methods and systems will benefit by using a first sidewall 54 that is narrower than a second sidewall 56, with the electromagnetic energy source directed through the first narrow sidewall 54. When the beam has a width that extends over across substantially all of the narrow sidewall 54, the entire cross section of the circulating test sample is irradiated. Directing the beam through the wider sidewall 56, on the other hand, would require a significantly wider beam (with resultant significantly lower per unit area energy).

Other configurations are possible to achieve this result, including, for example, test cell configurations with a narrow "throat" portion through which the test sample flows at a high velocity. The velocity should not be so great, however, as to shorten the residence time of analytes in the energy beam. One example configuration is discussed herein below.

It is also noted that there are benefits to locating the detection diaphragm 58 on the wider sidewall 56 through which the beam 64 does not pass. This wider sidewall 56 provides a larger area so that larger diaphragms 58 can be used. Also, in some experiments it was discovered that the beam 64 could cause increased noise in the detection signal by a pyro-electric effect of light photons interacting with the polymers of the film. Better performance was achieved when the beam was directed through the narrow sidewall 54 and direct interaction with the diaphragm 58 was avoided. In some example systems and methods, however, front excitation may be useful.

In other embodiments of methods and systems of the invention, another modification has been provided to further improve performance. Elements For adjusting the location of the laser beam 64 and the cell 52 relative to one another may be provided, for example. Although many possible mechanisms are possible to achieve this, an x-z translational stage connected to one or both of the laser 110 or cell 52 is useful. This can be useful to ensure the beam accurately encounters the test cell 52. Such a mechanism has been schematically illustrated as X-Y-Z adjuster 170. In practice this may comprise a controllable table underlying the laser 110 or cell 52 or the like.

Other potential modifications of the system 50 include using a fiber to communicate laser light as described above in order to maneuver the light source to the most efficient location for excitation of the cell 52. Trial runs were conducted using light emitted directly from a fiber and were found to result in a spot size of nearly 4 mm. It has been discovered that the focus of the laser light was important and directly related to signal strength. It has also been discovered that a small decrease in spot size diameter resulted in an increase in radiant exposure by the inverse square law. As discussed below, use of fiber was found, at least in the example system 50, to decrease signal intensity.

Radiant exposure is defined as Joules per $cm^2$. As it pertains to the design of some systems of the invention, a millimeter decrease in spot size from 3 mm to 2 mm for a 12 mJ light source results in a 125% increase in radiant exposure. Therefore, a 35 mm plano-convex lens (lens no. LA1027 from Thorlabs, Newton, N.J.) was inserted between the fiber and the detection chamber to decrease the incident spot size to approximately 2 mm in diameter. Eventually, the entire setup was repositioned for excitation without an intermediate fiber, as described above with reference to the laser system 110 and its lens 112. This increased incident energy from 7.0 or 8.0 mJ to 11.0 or 12.0 mJ. The spot size was brought to within 0.026 $cm^3$ (between 1 and 2 mm in diameter) giving a radiant exposure in the range of 460-900 $mJ/cm^2$ and increasing signal voltages to their highest level.

The amplification of the signal as it passes from the detection apparatus to the oscilloscope also can play an important role in the identification of a signal as well as noise response. In the example system 50, it was discovered that a gain of 25 appeared to produce the best signal differentiation. A gain of 125 often dropped the signal to noise ratio significantly and produced poor results, although it should be noted that in some instances a gain of 125 was preferable for the detection of extremely weak signals. Therefore, in the example system 50, a gain of 25 is used as a default, however, the gain should be set on the basis of the individual experiment or application.

Detection trials were run using the example system 50 and methods discussed above. Latex microspheres were used as a precursor to live melanoma cells. The test solutions were also used to determine a detection threshold for the example system and method in order to characterize the sensitivity of the example system. Some experimental runs were conducted using a dual chamber design while initial thresholding was performed using a single chamber design for the flow cell.

Black CML Latex Microspheres (no. 2-BK-7000 available from Interfacial Dynamics Corp., Portland, Oreg.) measuring 6.6 μm in diameter were used as tissue phantoms to mimic the photoacoustic response of melanoma cells (optical properties of melanoma cells and tissue phantoms are described below). The latex microspheres were chosen because of their broadband absorption spectrum and relative size. A standard melanoma cell can range between 10 μm to greater than 50 μm depending upon the heterogeneity of the cell line and morphology of the cell. Although the melanoma cell tends to be much larger than the microspheres used in these trials, the microshperes contain a darker pigment and therefore sufficiently imitate the photoacoustic effect of a melanoma cell, as discussed below. However, it is speculated that the larger size of the melanoma cells and the large number of melanin granules contained within them will allow them to produce a stronger photoacoustic signal than the microspheres per single cell. Therefore, it is believed that true melanoma will provide a signal similar to that of the microspheres, if not greater.

Spectroscopic analysis of the latex microspheres was conducted using a HR-2000 High-Resolution Spectrometer and a HL-2000 Halogen Light source (from Ocean Optics Inc., Dunedin, Fla.). An absorption spectrum of 4.3 g/100 ml (4.3%) black microspheres was taken using a 150 μm cuvette constructed of 1 mm thick glass slides (from Fisher Scientific, Pittsburgh, Pa.) and 150 μm shim stock (from Anus Corp., Englewood, N.J.). The microsphere solution was placed within the constructed cuvette and inserted between the halogen light source and detector of the spectrometer. Data was analyzed using OOIBase32 (from Ocean Optics Inc., Dunedin, Fla.). Data collection was taken under an integration time of 14 ms with no averaging. A short path length was used reduce the effects scattering on the absorbance data. The resultant absorption spectrum confirms that the microspheres possess steady absorption across the entire visible spectrum showing that the spheres are indeed a black broadband absorber. This spectrum indicates a slight increase in absorbency with wavelength within the visible range.

The latex microspheres were introduced into a signal conducting carrier fluid. In the experimental runs made, saline solution was used. Other carrier fluids will also be useful. Initially, the saline solution was a 0.9% sodium chloride (NaCl) solution created by adding 0.9 g of solid NaCl solute into 100 ml of de-ionized water solvent. In the experimental runs made, a 1.8% solution was used, although many other concentrations will be useful. Microspheres were added to 20 ml of saline solution in varying concentrations ranging from a maximum of $7.124 \times 10^6$ microspheres/ml to a minimum of $7.0 \times 10^2$ microspheres/ml. The microsphere concentration of each solution was deduced by:

$$\text{microsphere/ml} = \left(\frac{V_s}{V_m} \Big/ V_{su}\right)(V_i) / (20 \text{ ml})$$

where $V_S$ represents solid volume of microspheres from factory, $V_m$ volume of a single 6.6 μm microsphere, $V_{su}$ the remaining volume of factory microsphere suspension, and V; the volume incorporated into saline solution. 15 ml of each selected concentration was placed into the reservoir for circulation through the detection system.

Various concentrations of spheres were run using systems and methods of the invention. Trials employed a 0.9% saline solution, 510 nm excitation, 7.5 mJ input energy, and a 2.36 mm×2.45 mm spot size resulting in a radiant exposure of 0.129 J/cm². The signal was averaged over 64 acquisitions. Results of these tests confirm that systems and methods of the invention are not only useful to detect the microspheres, but further are useful to estimate concentration of the microspheres.

Two additional sets of experiments were conducted to determine the sensitivity of one example system and method. In the first, sample concentrations ranging from $7.12 \times 10^6$ to $7.0 \times 10^2$ J 1 spheres/ml were used to gain an understanding of signal variation with concentration. Determining this makes it possible to quantify unknown concentrations of tissue phantoms by known signal intensities. This represents an important benefit of some systems and methods of the invention—signal intensity can be used to estimate qualities such as analyte density, analyte concentration, analyte size, and other properties.

All trials in the first set of experiments were run with the following experimental parameters: 450 nm excitation, 8.75 mJ energy input, 1×1 mm spot size, 13.1, mm beam length, radiant exposure of 0.875 J/cm², and 9 ml/min flow rate. Samples $7.12 \times 10^6$ through $8.9 \times 10^4$ employed a signal gain of 25 averaged over 64 acquisitions. Lower concentrations ranging from $5.5 \times 10^3$ through $7.0 \times 10^2$ used a signal gain of 125 averaged over 128 data acquisitions. The differing parameters were useful to differentiate signals of lower concentrations for this setup. The experimental results of these experiments again confirmed that photoacoustic detection of circulating cells can be achieved using systems and methods of the invention as described herein. Latex microspheres, 6.6 μm in diameter, were successfully detected at 3 concentrations on the order of $10^6$ per milliliter.

In the second set of experiments seven microsphere solutions of different concentrations ranging from $8.9 \times 10^4$ μs sphere/ml to $7.0 \times 10^2$ μs sphere/ml were passed through a system of the invention. Trials were run with the following parameters: 450 nm excitation, ×25 amplification, averaged over 128 data acquisitions, flow rate of 9 ml/min, laser energy input 11.5-12.0 mJ, spot size of 0.13×0.2 cm (0.026 cm²), and a radiant exposure of 0.461 mJ/cm².

These experiments suggest that variations in signal amplification gain may be one example parameter modification useful to increase sensitivity. In the example system 50, gains of 25, 50 and 125 were found useful. Higher gain settings resulting in greater detection sensitivity. Too high of a gain setting, however, risks a high signal to noise ratio.

In further consideration of sensitivity, assuming even distribution of microspheres within the entire solution, the exact amount of single microspheres crossing the beam path at any given time can be deduced by:

$$M_\# = (C_m)(V_b)$$

Where $M_\#$ is the number of excited microspheres, $C_m$ is concentration of microspheres per milliliter solution, and $V_b$ is the volume of the excitation beam path through the flow cell in cm³. This deduction makes it possible to realize the number of single cells producing each photoacoustic signal, therefore interpolating the number of single chromophores necessary to induce a differentiated signal.

Also, during the experimental trials a more concentrated saline solution was used to boost signal strength by increasing conductivity throughout the test solution while decreasing resistance from water. Initially, a physiological saline solution of 0.9% had been used as a solvent for trials. A study was conducted that doubled the saline concentration to 1.8% with a resultant increase in signal strength. Increasing the saline concentration from 0.9% to 1.8% increased the peak signal of a solution by a factor of 1.2. Although further increases in strength may be achieved with higher saline concentrations, at some level the concentration becomes too high to support a live melanoma cell survive, since they begin to lyse at saline concentrations of above about 0.9%. It is believed that concentrations of about 1.8% provide a useful maximum, although in some circumstances higher concentrations may be utilized. Also, other solutions in addition to saline may be useful in practice of methods and systems of the invention. Generally, conducting fluids that support a melanoma will be useful when using an acoustic sensor that relies on an internal electrode. Other sensor configurations may allow for non-conducting fluids to be used.

Using the example system discussed above with a 1.8% saline solution carrier was shown to be very successful for the photoacoustic detection of tissue phantoms in the form of 6.6 μm black latex microspheres. The results indicate that systems and methods of the invention are capable of detecting the presence of single cells in a circulating solution.

In order to further characterize some systems and methods of the invention, further testing was performed using analytes other than or in addition to the above described microspheres. An application that many systems and methods of the invention will find particular utility include (but are not limited to) detecting cancerous melanoma cells circulating within the hematogenic system of a potential cancer patient. The example detection systems and methods of the invention can process materials through in vitro analysis which requires a method for extracting the cells of interest from a human patient. A simple blood draw is the most common method for obtaining cells present in the circulatory system and may be used as a relatively pain-free, routine method for obtaining particular samples of interest. Once a blood sample is collected, it is proposed that metastatic melanoma cells can be accurately isolated from whole blood in vitro by implementing, by way of example, a Ficoll-Hypaque centrifugation technique. This technique requires the extracted whole blood to undergo centrifuge gradient separation in order to isolate the particular cell layer of interest before introducing it to the photoacoustic detection system.

To further evaluate systems and methods of the invention, tissue phantoms representing biological melanoma were introduced into healthy samples of blood in vitro and detected using the photoacoustic method. This section describes experimental details of such test runs. Before providing such detail, however, some application background will be helpful.

Leukocytes, or white blood cells, defend the body against infecting organisms and foreign agents, both in tissue and in the bloodstream itself. Human blood contains about 5,000 to 10,000 leukocytes per cubic millimeter; the number increases in the presence of infection. Leukocytes as well as erythrocytes are formed from stem cells in the bone marrow. They have nuclei and are classified into two groups: granulocytes and agranulocytes.

Granulocytes form in the bone marrow and account for about 70% of all white blood cells. Granulocytes include three types of cells: neutrophils, eosinophils, and basophils. Neutrophils constitute the vast majority of granulocytes. The main purpose of these cells is to surround and destroy bacteria and other foreign particles as well as act in inflammatory response mechanisms during infection or allergic reaction. Granulocytes serve as the first line of defense against infection by foreign cells.

Agranulocytes include monocytes and lymphocytes. Monocytes are derived from the phagocytic cells that line many vascular and lymph channels, called the reticuloendothelial system. Monocytes ordinarily number 4% to 8% of the white cells. They move to areas of infection, where they are transformed into macrophages, large phagocytic cells that trap and destroy organisms left behind by the granulocytes and lymphocytes. Lymphocytes, under normal conditions, make up about 20% to 35% of all white cells, but proliferate rapidly in the face of infection. There are two basic types of lymphocytes: the B lymphocytes and the T lymphocytes. B lymphocytes tend to migrate into the connective tissue, where they develop into plasma cells that produce highly specific antibodies against foreign antigens. Other B lymphocytes act as memory cells, ready for subsequent infection by the same organism. Some T lymphocytes kill invading cells directly; others interact with other immune system cells, regulating the immune response.

Peripheral Blood Mononuclear Cells (PBMCs) is a term used to describe monocytes and lymphocytes that can be separated from a whole blood solution using a Ficoll-Hypaque centrifugation technique described herein. Other separation techniques, including centrifuge and similar techniques, will also be useful with methods and systems of the invention.

Although conflicting information exists on metastatic disease and its interactions with the human immune system, it is hypothesized that antigens present on the surface of melanoma cells within the blood stream of an individual with metastatic disease will be recognized and bound by these mononuclear cells. This assumption is based upon the idea that metastatic disease is a chronic disease which persists in the blood stream and would be primarily attacked by monocytes and lymphocytes that are thought to defend against chronic illness more so than granulocytes. Therefore, isolation of the peripheral blood mononuclear cell layer should result in the isolation of any melanoma cells present in the blood stream.

Samples of healthy, cancer free blood were drawn from consenting individuals from within the lab group. Samples were taken by venipuncture from the antecubital area of the arm in the amount of 10-50 cubic centimeters using a standard blood draw procedure. Ethylenediaminetetraacetic acid (EDTA) liquid coated tubes were used for blood collection to inhibit clotting. Blood samples were stored in a refrigerated environment for no more than five hours before being processed.

A Ficoll-Hypaque separation technique was used to isolate the peripheral blood mononuclear cell layer from the whole blood samples. The Ficoll-Hypaque process employs a sugar compound of a specific density that separates specific blood components by a density gradient when centrifugal force is applied. Approximately 1 ml of Histopaque 1077 (from Sigma-Aldrich Inc., St. Louis, Mo.) separation gradient was placed in Pyrex No. 9800 glass tubes (from Corning Inc., Acton, Mass.). Approximately 7 ml of blood from the refrigerated samples were gently poured on top of the Histopaque 1077 and stopped with a rubber stopper. The sample tube was then placed in a 60 Hz 3400 rpm Vanguard 6500 centrifuge (from Hamilton Bell Co., Montvale, N.J.) and spun for 10 minutes. The resulting gradient and relative location includes the peripheral blood mononuclear cell layer consisting of monocytes and lymphocytes separated out directly above the Histopaque layer and below the plasma. The Granulocytes are larger and separate below the Histopaque layer, directly above the blood layer (not shown).

Following separation, the differentiated PBMC layer was carefully removed using standard transfer pipets (from Samco Scientific Corp., San Fernando, Calif.) and placed into 1:5 ml Flat Top Microcentrifuge Tubes (from Fisher Scientific, Pittsburgh, Pa.). The PBMCs in the micro centrifuge tubes were washed in a saline solution and re-spun for 5 minutes. Excess saline solution and plasma was pipetted off of the top of PBMC layer. This was repeated until peripheral blood mononuclear cells were cleanly isolated.

Two suspensions of isolated mononuclear cells (0.111 g) were added to 20 ml of a 0.9% saline solution. One suspension served ace; the control. The second suspension contained 0.5 ml ($1.49 \times 10^8$) of black latex microspheres. Both were introduced to an example photoacoustic detection system of the invention.

A second test sample was created in which 1 ml ($2.98 \times 108$) of 6.6 μm black latex microspheres was added to 7 ml of human blood sample prior to FicollHypaque centrifugation. Peripheral blood mononuclear cell layer was isolated as previously described, added to 20 ml of 0.9% saline, and introduced into detection system.

All trials were run with the following parameters: 450 nm excitation, amplification ×25, averaged over 128 data acquisitions, 9 ml/min flow rate, 9.5-10.5 mJ input energy, and a spot size of 0.16×0.16 cm (0.0256 cm$^3$) resulting in a radiant exposure of 0.39 J/cm$^2$. It is postulated that melanoma cells in the blood stream of a metastatic patient may remain in the plasma when subjected to the Ficoll-Hypaque gradient. For this reason, a separate trial was conducted using isolated blood plasma to determine the dynamic ability of the example detection system to function using different mediums. Two samples were prepared, a control sample consisting of 3 ml of human plasma and 10 ml of 0.9% saline and a test sample of the same solution with 0.5 ml (1.49×108) black microspheres added, to mimic the presence of melanoma in plasma. Similar experimental parameters were used as before, only a 595 nm excitation wavelength was used to eliminate absorption by the naturally yellow pigmented plasma. After isolation of the peripheral blood mononuclear cell layer, a saline/mononuclear cell suspension was made to which $1.49\times10^8$ microspheres ($7.12\times10^6$ per ml) were added. Amplification was set at 25, 450 nm excitation, and photoacoustic results for a control agranulocyte cell suspension.

The resultant output control waveform for the mononuclear cell suspension confirms that there is no photoacoustic excitation that occurs from exciting the PBMCs. This is expected since mononuclear cells are white in color and should contain no active chromophores that may produce a photoacoustic signal. The photoacoustic waveform resulting from the addition of microspheres to an isolated mononuclear cell suspension once again clearly confirms the ability of example systems and methods of the invention being investigated to identify chromophores amongst a circulating PBMC solution.

Also, the waveform resulting from the addition of microspheres to whole blood previous to centrifugation is representative of melanoma cells present in the blood stream itself. The microspheres were added in large concentration so that if all the spheres were isolated properly, $7.12\times10^6$ μs spheres/ml would result in solution. This was most likely not the case as it can be assumed that many microspheres were lost during the process of separation. The resulting waveform shows that Ficoll-Hypaque centrifugation is extremely successful in isolating tissue phantoms representing melanoma cells, proving this hypothesis correct.

The extraction of blood plasma illustrates a second method for detecting chromophores amongst a non-saline solution. Microspheres were accurately detected at high concentrations at 595 nm. This shows the versatility of wavelength modification for detection. 595 nm does not excite the yellow pigmented plasma (as seen in the control) primarily because plasma absorbs in the blue and red spectrum. Still, 595 nm provides photoacoustic excitation for tissue phantoms present in solution due to the broadband absorption of the microspheres. This provides a mode for detection of cells isolated to the blood plasma, which will prove beneficial.

These experiments confirmed that photoacoustic response from tissue phantoms inoculated into healthy blood can be accurately isolated and detected using photoacoustic detection systems and methods of the invention illustrated above. Experimental results confirm that methods and systems of the invention are useful to extract and identify cells evenly distributed amidst hundreds of millions of blood constituent cells not of interest. It also shows the ability of the systems and methods to express the presence of chromophores amongst a mononuclear cell suspension which eliminates the need for a further cell isolation method. It is believed that live malignant melanoma cells will reside in the same FicollHypaque gradient as the tissue phantom cells. However, it is also possible that the melanoma cells, being larger than the microspheres and of different makeup, may separate differently, possibly to the granulocyte layer.

Detection trials described above have shown that example methods and systems of the invention can successfully detect chromophores in solution on the order of twenty single cells or fewer. The sensitivity of one example system described above is as low as two microspheres. Other systems and methods of the invention can be modified through selection of laser energy, beam area, test cell geometry, and similar parameters to achieve a detection threshold of as low as one cancer cell.

An additional experimental evaluation of methods and systems of the invention in applications directed to the detection of disseminated cancer cells is to test the ability to detect melanoma cells in vitro. In order to do so, a live melanoma cell line was cultured so that an abundance of isolated melanin could be introduced into the system for detection. The below discussion describes the cell line used and cell culturing methods employed, and describes in detail methods and systems of the invention used for detecting the live melanoma.

Some background discussion on melanoma will be useful. Melanoma is a malignant tumor composed of unregulated melanocytes. A melanoma cell is essentially a melanocyte containing one or more mutations that inhibit normal cell growth and regulation. A melanocyte produces coloring in mammals by secreting three unique pigments: the dark insoluble, nitrogenous eumelanins formed from the oxidative polymerization of dihydroxyindolequinones, the sulphur-containing alkali-soluble phenomelanins derived from cysteinyl-DOPA which provide the lighter colors (primarily brown and red-brown), and the amphoteric pheochromes (red and red-orange colors). These colors are enzymatically synthesized by 10 nm granular sites studding the internal walls of the melanocytes.

These pigments are termed melanin and are produced in various shapes, sizes, and amounts depending upon the cell. The amount and type of melanin produced determines skin, hair, and eye color in mammals. The melanin produced is encapsulated by the melanoma cell providing a pigment for any cell producing melanin. It is the melanin granules encapsulated within the melanocyte, or melanoma cell, that serves as the broadband absorber to produce photoacoustic signals when exposed to incident laser light.

Melanins are a broad class of functional macromolecules that together exhibit a band structure model characteristic of an amorphous solid with broad band absorption spectrum in the visible and UV. Eumelanin, the prevalent pigment, has been shown to efficiently absorb UV and visible photon energy and deactivate with a quantum efficiency of less than 0.05%, which fits its role as a photoprotectant in skin. The mechanism by which this occurs is complicated and not entirely understood. Studies show that melanins consist of small heterogeneous oligomeric units that possess different redox states resulting in a broad range of HOMO-LUMO gaps (energy difference between the highest occupied molecular orbital and the lowest unoccupied molecular orbital). This chemical disorder model allows for broadband monotonic absorption as a consequence of the superposition of a large number of non-homogeneously broadened Gaussian transitions associated with the components of the melanin ensemble. Despite all the work done to characterize melanin absorption it has been hypothesized that the absorption spectrum of human melanin is dominated by scattering, as it shows no characteristic absorption resonances in the visible or ultraviolet.

Melanocytes are present in all epithelial based organs which give rise to cancerous tumors. It is therefore believed that melanoma cells are present in any epithelial based cancers, or carcinomas, and their resulting metastatic cells. Unfortunately, approximately 10% of these carcinomas consist of amelanotic melanoma cells that do not produce pigment therefore rendering the photoacoustic detection method ineffective. It is believed, however, that molecular tagging mechanisms, including dyeing and nanoparticle technology by way of example and not limitation, could be used to identify and bind to amelanotic cells in vitro which would allow for photoacoustic excitation of the bound markers. This could eventually allow for the photoacoustic detection of any melanoma based cancer.

The Melanoma cell line utilized in experiments discussed below was SK-MEL-1. These cells were originally obtained in 1968 from the thoracic duct lymph of a 29 year old Caucasian with rapidly progressing malignant melanoma. The cells are known to be tumorigenic in nude mice or cortisone treated hamsters, producing pigmented malignant melanomas. Additional cellular characteristics included a spherical growth property, with cells loosely clustered exhibiting a granular cytoplasm.

The cells were grown in suspension in 25 $cm^2$ Canted Neck Flasks with a Phenolic Style Cap (from Corning Glass Works, Corning, N.Y.) at 37° C. in a humidified 5% $CO_2$ environment. Approximately 10 ml of the cell suspension was kept in each flask. A media composed of 444.4 ml RPMI (from Invitrogen Corp., Grand Island, N.Y.), 5 ml Glutamine (also from Invitrogen Corp.), 50 ml Fetal Bovin Serum (from U.S. Rio-Technologies Inc., Pottstown, Pa.), and 0.6 ml Gentamycin (from American Pharmaceutical Partners, Schaumburg, Ill.) was used and renewed three times per week. When changing the media, 7 ml of the cell suspension was removed and discarded, leaving 3 ml in the original flask. Then, 7 ml of fresh media was then added back to the flask.

The cells were counted before each media renewal. A small sample of cells would be obtained for the count. The cells were gently mixed with a blue ink at a dilution of 1:2. Using a hemacytometer, the cells in three squares were counted. A cytospin was performed on a selected batch of cells and a cell block was made and stained with Hematoxylin and Eosin. Individual cells varied in size, with many containing dark, intracellular inclusions. The nuclei were centrally located, round, and contained one or more prominent nucleoli.

The amount of melanin produced was found to vary by cell with approximately 5% of the cells containing dense brown cytoplasmic granules dispersed evenly throughout the cytoplasm. Therefore only 1 in 20 live melanoma cells were actively producing melanin. Mutated aneuploid state of the transformed melanoma is apparent through cells containing multiple nuclei.

A number of control trials were run using example methods and systems of the invention in order to definitively prove the detection of melanoma cells as opposed to other absorbers or pyro-electric effects. These control experiments were run in addition to detecting melanoma suspensions.

In addition to a plain 1.8% saline control solution (as prepared and tested in above discussion), a $7.124 \times 10^6$ μs sphere/ml solution was prepared using 6.6 μs White CML Latex Microspheres (from Interfacial Dynamics Corp., Eugene, Oreg.). Whereas black microspheres represents the absorbing effects of melanoma, white microspheres can be used to represent the scattering effects of melanoma cells. Therefore, the white microsphere suspension was introduced to determine the effects of a purely scattering medium on the system. Live melanoma cells act as both absorbers and scatterers due to their variable melanin content and large amount of while surface area. It is possible that a scattering medium (such as melanoma) may produce phantom signals or oscillations due to a pyro-electric effect, or signals produced by scattered photons interacting with the piezoelectric film or electrodes. These control trials give examples of typical pyro-electric waveforms so as to eliminate the possibility of mistaking a pyro-electric signal for that of a melanoma signal.

A second control experiment was conducted using a 1:1 suspension of RPMI Culture Medium (discussed above) and 1.8% saline. The medium, used to culture the melanoma cells, contains phenol red that serves as an acid/base indicator to identify when the cells have expired the nutrients of the growth medium. Phenol red (Phenolsulfonephthalein) has a pK value of 7.9. Different absorption spectra exist from different sources and detection techniques as can be seen by comparing the two spectra. It is evident that phenol red has a variable absorbance at 450 nm that could produce a photoacoustic signal but no absorbance at 620 nm. Therefore, detection trials were ran at 450 nm and 620 nm for both the culture medium suspension and the melanoma suspension for comparison. This would ensure that any signal produced at 620 nm would be that of the melanoma cells not that of the culture medium either present on the cells or absorbed by the cells. Thus eliminating the notion that the culture medium may be producing a photoacoustic signal mistaken for melanoma.

Before suspending the melanoma for introduction into the detection system, the cells were counted then spun at 1200 RPM at 4° C. for ten minutes using a Fisher Scientific accuSpin 3R centrifuge. The supranatant of media was then removed from the cell pellet formed. Next, the cells were washed using Dulbeccos Phosphate Buffered Saline (Invitrogen Corp., Grand Island, N.Y.). Saline was added to the pellet, the cells were gently mixed, becoming again suspended, and the procedure was repeated using the same methods as described above. Finally, the supranatant of saline was removed, and a small amount of fresh saline was added to the cell pellet.

A 15 ml solution was made consisting of $2.3 \times 10^6$ live melanoma cells and 1.8% saline resulting in a $1.53 \times 10^5$ cell/ml suspension. This suspension was entered into the example system of the invention and detected using pulsed laser light with the following parameters: 450 nm and 620 nm excitation, 9.5-11.6 mJ input energy, gain of 25, and averaging over 128 data acquisitions.

The cell line chosen for these trials was a non-clustering metastatic melanoma cell line. The original sample was taken from the metastatic tumor of a class IV cancer patient which insinuates that the cells possess an inherent ability to disseminate and intravasate into the blood stream. Therefore, the cells cultured and tested should be comparable to cells that would be present in the blood stream of a metastatic cancer patient. Approximately 5%, or 1 in 20, of the cultured cells produced visible melanin. The irradiated spot size for these trials was 0.13 cm×0.2 cm (0.026 $cm^2$) with a beam length of 1 cm. If it is assumed that 1 in 20 cells produced viable melanin then it can be deduced that any resulting signal was produced by 200 melanotic melanoma cells per irradiated beam path. 450 nm was used to excite the melanoma samples due to the optical absorption properties discussed above.

Figure 7:
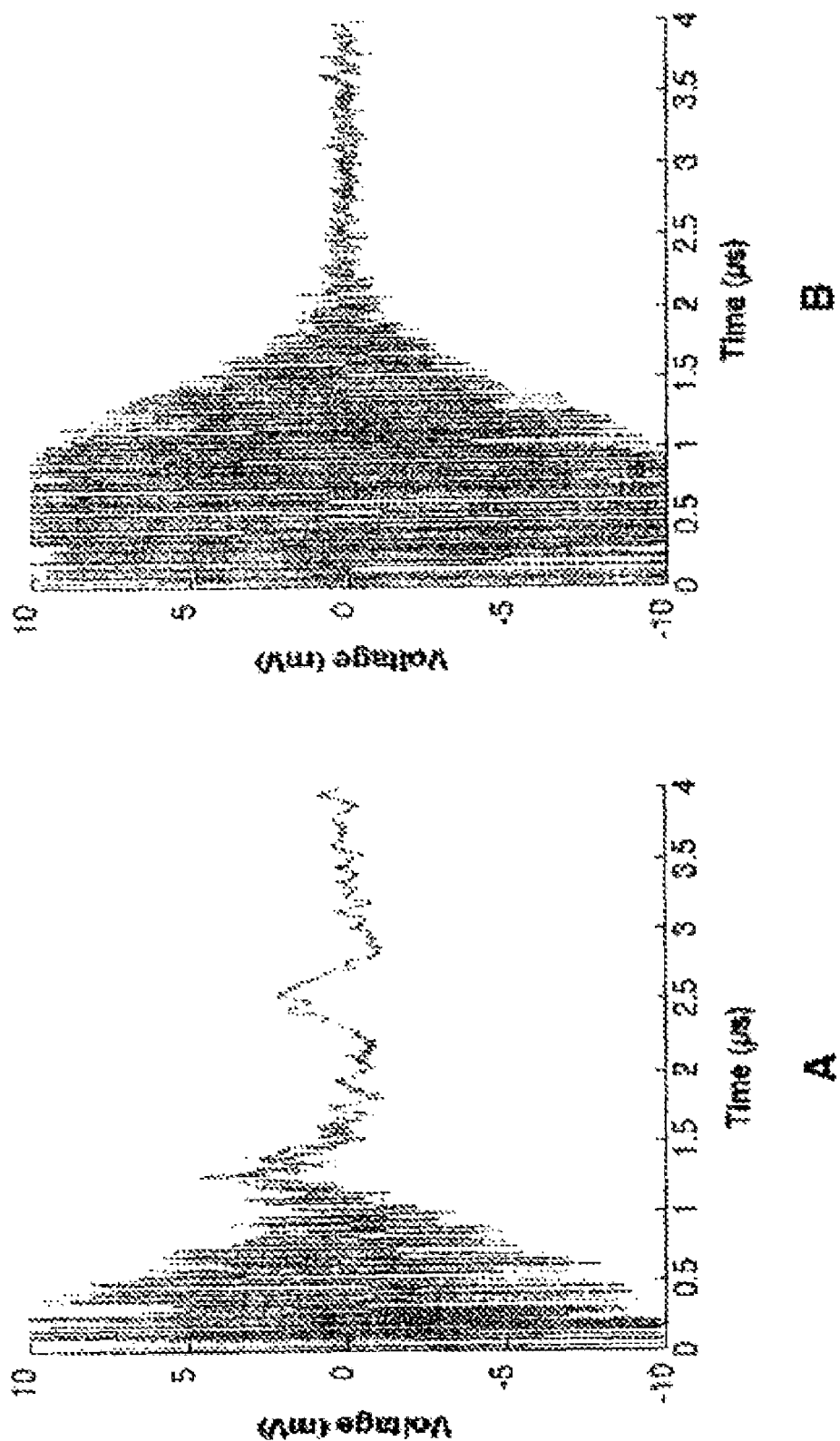
FIG. 7 illustrates data resultant from practice of an example system and method of the invention, with FIG. 7(A) data for a test sample including live melanoma and FIG. 7(B) data for a test sample including RPMI culture medium and no melanoma.

FIGS. 7A and 7B show resulting data, with FIG. 7A including results for the live melanoma and FIG. 7B showing results for RPMI culture. Noise data at the far left of each plot (near the origin) corresponds to noise from firing of the laser. As indicated by FIG. 7A, a distinct melanoma signal is evident at about 2.5 ms. No such peak occurs in the RPMI data of FIG. 7B. The results of these experiments confirm that live melanoma signals were clearly and consistently differentiated. The signals were clearly unique from those of the RPMI culture medium and the microsphere tissue phantom trials. These characteristic waveforms clearly show the ability of the detection system to detect malignant melanoma cells in vitro.

Cultured live malignant melanoma was therefore successfully detected using systems and methods of the invention. The signals were clearly differentiated and retained a distinct pattern relating to melanoma detection. Also, when compared to the threshold trials for the example methods and systems discussed above in relation to testing for spheres only, the melanoma signal was more than a 2 fold increase in voltage.

The determination of optical properties for the black latex microspheres and live melanoma cells discussed above is useful to the understanding of how the microsphere tissue phantoms compare to the live cells they are trying to represent. Understanding how light interacts with the two absorbing mediums tested allows for conclusions to be drawn regarding their abilities to produce photoacoustic signals. Once the signal production potential is realized through the determination of optical properties, the photoacoustic response of both the melanoma cell suspensions and the black latex microsphere suspensions can be further explained. From this data correlations can be made between the sensitivity trials conducted with latex tissue phantoms and the results from actual live melanoma detection.

Integrating spheres offer a method of simultaneously determining the optical properties of materials by employing the Inverse Adding-Doubling Algorithm to measured light flux gathered from the integrating spheres. This discussion details the optical properties of interest, provides a brief explanation of the theory of integrating sphere measurements, describes the methodology used, and discusses the optical properties of the latex microspheres and malignant melanoma.

There are a number of properties that are used to describe light interactions with turbid media. The three properties considered in detail herein are absorption, scattering, and anisotropy. One important optical property for the purpose of the systems and methods of the invention is absorption. The amount of absorption of a material at a particular wavelength is directly related to the strength of the photoacoustic signal that it produces.

Absorption occurs when an incident light photon interacts with a molecule that can absorb that photon in the form of molecular energy transition. In the visible spectrum these transitions consist of electron orbital shifts in compounds composed of conjugated dienes. Compounds containing conjugated dienes make up the majority of absorbing materials, or chromophores. The absorption of a compound is described by its absorption coefficient, $\mu_a$ defined as the probability of light absorption in an infinitesimal distance ds, given as $cm^{-1}$. The absorption coefficient is wavelength dependent and is determined by the type of chromophore and its concentration. Assuming a purely absorbing medium, the absorption coefficient can be calculated using Beer's Law given as:

$$I_tI_oe^{-\mu_a d}$$

The absorption coefficient is exponentially related to the percentage of transmitted light and dependent upon the thickness of the sample. This describes the simplest method of determining absorption. Realistically, a purely absorbing medium does not exist thus explaining the need for more complicated methods of optical property determination such as the inverse adding-doubling algorithm.

Scattering describes the interaction of photons that are not absorbed by a particular medium and is caused by changes in the index of refraction across a material. Optical scattering is described by the scattering coefficient, $\mu_s$, and defined as the probability of photon scattering in an infinitesimal distance ds, given by $cm^{-1}$. The scattering coefficient of a material is based on the volume density of scatterers and is dependent upon the size of the particle. Beer's Law can be used in the same manner as absorption for calculating the scattering coefficient for a purely scattering medium.

Anisotropy describes the amount of light that is forward scattered by a material. The phase function, or angle of light refraction, is characterized by anisotropy, g, which is the average cosine of the phase function. Anisotropy varies between isotropic scattering (g=0) and complete forward scattering (g=1).

There are other optical properties that may be relevant to some methods and systems of the invention, including, for example, the scattering albedo given by:

$$\alpha = \mu_s/(\mu_a + \mu_s)$$

The albedo represents the relative portion of scattering during a light interaction event. The total light attenuation coefficient is given by:

$$\mu_t = \mu_a + \mu_s$$

The effective attenuation rate for highly scattered media is given by:

$$\mu_{eff} = \sqrt{3}\mu_a(\mu_a + \mu_s(1-g))$$

The mean free path (mfp) for a photon passing through an absorbing and scattering medium is given by:

$$mfp = 1/\mu_t$$

The optical depth for an absorbing and scattering medium is given by:

$$\tau = d(\mu_a + \mu_s)$$

Finally, the reduced scattering coefficient describes a highly scattering medium by relating anisotropy to the scattering coefficient as:

$$\mu_a' = \mu_s(1-g)$$

All of these optical properties can be used to decipher the composition of a material through practice of systems and methods of the invention.

These relationships can be used not only to better understand the operation and results of systems and methods of the invention, but may also be used to determine and estimate qualities of detected analytes. Steps of a method of the invention include, for example, using these relationships to determine an analyte density, mass, size, concentration, and the like.

Also, some other example methods and systems of the invention may includes steps and elements for building a knowledge base over time that is useful to determine such characteristics for analytes. By way of example, some methods of the invention may include steps of calibration whereby different phantom targets (e.g., microspheres) are tested using different concentrations, different absorbance, different energy input, and other test parameter variations. A system of the invention may include a memory for storing resultant data and program instructions for analyzing the data. The resultant data can be used to develop a predictive model to use when actual test data from an unknown analyte is presented to determine characteristics of that analyte.

Also, so called signature waveforms can be developed for different analytes through testing. These can be useful to identify an unknown analyte. Further, some systems and methods of the invention may be useful to detect and identify multiple different analytes in a single sample. The different analytes present in the single sample can be identified through their different waveforms.

Photoacoustic detection systems and methods of the invention have the ability to detect the presence of melanin in solution. Example systems and methods are easy to use and allow for relatively simple sample preparation in that once a cell block is isolated, only a carrier fluid such as saline is required to be added in order to conduct the voltage signal. Samples can be quickly introduced to an example system via an external reservoir and circulated using a pump to induce negative pressure. The test solutions can also be easily removed and the entire system can be cleaned in minutes providing efficient results and the capacity for high volume processing.

Those knowledgeable in the art will appreciate that many modifications to example systems and methods discussed above can be made. For example, detection chambers may be configured to improve upon the sensitivity of the device. Example systems and methods of the invention have been used with phantoms in the form of 6.6 μm Black CML Latex Microspheres, which act as a broadband absorber similar to that of melanin. Photoacoustic signals derived from black latex microspheres have been discriminated and have shown a low detection threshold as well as a very strong and clearly differentiated signal.

Methods of the invention also include steps for the isolation of melanoma cells from whole blood. It has been discovered that the peripheral blood mononuclear cell layer can be isolated and placed in the detection system without creating false positives. Also, the simple addition of tissue phantoms in the form of latex micro spheres to whole blood has produced strong results indicating that the protocol for sample preparation can accurately isolate foreign bodies, such as melanoma, in the blood stream. Results have proven successful in detecting broadband absorbers in the midst of millions of mononuclear cells.

An example photoacoustic device of the invention has successfully detected live melanoma cells in a standard saline suspension. The photoacoustic waveform for malignant melanoma is markedly different from that of other absorbers including the tissue phantom microspheres. Acoustic diffraction by the melanoma cells results in a uniquely identifiable photoacoustic waveform that can be used to differentiate a melanoma signal from potential false positives such as blood. Detection threshold is of a useful level to provide very early detection of CTC's, pathogens, and other analytes of interest. In addition, modifications to the some elements of the systems and methods described herein are contemplated to increase sensitivity. Such modifications include, for example, increasing the incident beam intensity or size, decreasing irradiation area, further improving signal strength, and the like.

Figure 8:
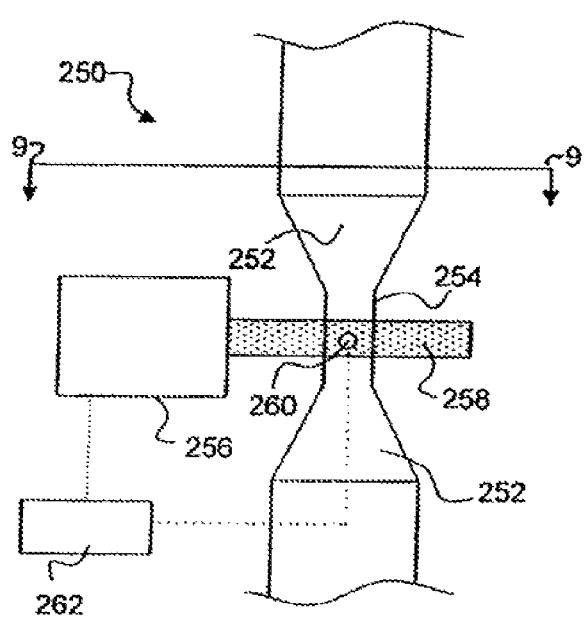
FIG. 8 is a schematic illustration of an alternate example flow cell.
Figure 9:
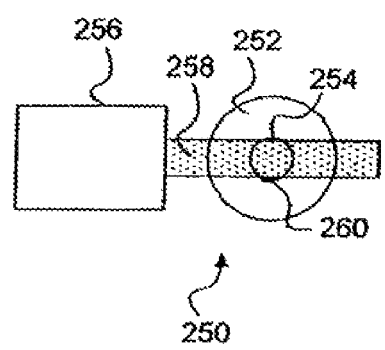
FIG. 9 is a schematic illustration of the flow cell of FIG. 8 viewed along the line 9-9 of FIG. 8 in the direction shown.

FIGS. 8 and 9, for example, schematically illustrate one example alternate configuration of a flow cell 250. The cell 250 includes upper and lower sections 252 that are generally funnel shaped. A cylindrical shaped narrow throat section 254 is located between and connects the two funnel sections 252. The throat section is made of a transparent sidewall that may be glass, by way of example. A laser 256 directs a pulsed beam 258 through the throat section 256. As best shown by the overhead view of FIG. 9, the pulsing beam 258 extends across substantially the entire diameter of the cylindrical throat section 254 whereby an entire cross section of the test sample being communicated through the throat section 254 is illuminated. Put another way, this configuration, like that of FIGS. 3-5, captures the entire flow of the test sample within the beam path.

An acoustic sensor 260 is arranged on a side of the throat section 254. The sensor 260 may be a film that is deflected when an acoustic wave strikes it, or may be another device. As shown in FIGS. 8 and 9, the sensor 260 is arranged on the throat section 254 at a location adjacent to the path of the beam 258, but is located on a side where the beam does not directly pass to avoid (or at least minimize) potential interference with or from the laser beam 258.

The flow cell 250 may be dimensioned as desired and as is suitable for a particular application. In one example configuration, the cell is in a micro scale so that the throat section 254 transports only a few melanoma cells and guarantees excitation of all material passing through the section 254. The throat section 254 may be, for example, a capillary tube having a diameter of about 1 mm or about 2 mm. If provided in a suitably small diameter, only one or a few CTC's would be expected to be in the small volume resident in the throat section 254. Directing the energy beam 258 at the narrow throat 254 would then excite only a singe or a few CTC's at a time.

Using a configuration such as the flow cell 250 may be useful in some methods of the invention to estimate analyte concentration. Wave spikes in the resultant data can be counted to estimate the number of analyte cells detected in the sample. This knowledge together with the volume of the sample will lead to a determination of the analyte concentration in the sample.

The flow cell 250 may be placed in line with a reservoir, a pump and other elements as desired. It may be used in a circulating configuration wherein a sample is passed through the throat section 254 multiple times, or it may be used in a single pass configuration wherein a sample passes through the flow cell 250 only a single time. In one example configuration, the flow cell 250 is used in a gravity flow arrangement that does not rely on a pump. Or, a syringe can be used to deliver a test sample in line with the flow cell 250, with the ejecting pressure from the syringe urging the test sample through the cell 250. A controller 262 (FIG. 8) is provided and linked to both the laser 256 and to the acoustic sensor 260. The controller may be a processor based device such as a computer, and includes data acquisition processing, data storage, laser control, and acoustic sensor control functionalities. It can also include a display for displaying data.

The detection systems and methods of the invention for detection of analytes such as metastatic melanoma have proven to be successful. With the ability to analyze blood samples within 30 minutes without the aid of a trained histologist, an example photoacoustic detection system may prove to be the most reliable method of detecting cancer. This unprecedented method and system could revolutionize the field of oncology, among others, by providing a vehicle for the early detection of metastatic disease as well as functioning as a method for determining the effectiveness of chemotherapeutics. In addition, if the parallel theory of metastasis holds true, example devices and systems will be of great utility as early detectors of not only metastatic disease but any melanotic form of cancer near its inception.

Methods and systems of the invention are not limited to cancer or pathogen detection, however. Those skilled in the art will appreciate that systems and methods will find utility in a wide variety of other applications. Some additional example applications include testing to determine if a body fluid includes a particular protein or a trace of an illegal drug. Others include detecting analytes that are present in sperm.

The benefits and advantages of devices and systems of the invention are evident. Discussion herein of particular example methods and systems has been made for purposes of illustrating some best modes for practicing the invention. The scope of the invention as defined by the attached claims, however, is not necessarily limited to the particular elements shown and discussed. Modifications, equivalents and alternatives to the systems and methods will be apparent to those skilled in the art.

The invention claimed is:

1. A system for detecting one or more analytes in a bodily fluid comprising:
a test chamber having at least one sidewall and configured to contain at least a portion of a bodily fluid sample;
an electromagnetic energy source configured to direct an energy source into said test chamber through said at least one sidewall and to induce a thermoelastic expansion in said one or more analytes; and,
a sensor configured to detect said thermoelastic expansion in said bodily fluid sample in said test chamber, said sensor comprising an acoustic sensor having a diaphragm that is deflected when an acoustic wave generated by said thermoelastic expansion strikes it, said acoustic sensor arranged on said test chamber, wherein a first side of said diaphragm is configured to be in fluid contact with the bodily fluid sample and an opposing second side is configured to be exposed to the environment.

2. A system as defined by claim 1 wherein said electromagnetic energy source comprises a laser pulsing at a frequency faster than a millisecond.

3. A system as defined by claim 1 and further comprising:
a reservoir, a conduit, and a pump, said reservoir communicating with said test chamber via said conduit, said pump arranged along said conduit to urge said sample from said reservoir to said test chamber;
wherein said electromagnetic energy source comprises a pulsed laser; and,
wherein said test chamber at least one sidewall comprises at least a first and a second sidewall, said first sidewall being narrower than said second sidewall, said pulsed laser directed through said first sidewall and said sensor arranged on said second sidewall.

4. A system as defined by claim 1 and wherein said test chamber is transparent and wherein said electromagnetic energy source comprises a pulsed laser having a beam that illuminates an entire cross section of said test sample as it passes through said test chamber.

5. A system as defined by claim 1, wherein the test sample flows through the test chamber, and wherein said electromagnetic energy source is configured to direct a first energy beam having a first wavelength but not a second wavelength, and at a different time to direct a second energy beam having the second wavelength but not the first wavelength into the test chamber, the first energy beam inducing a first thermoelastic expansion in a first analyte that absorbs the first wavelength but not the second wavelength, the second beam inducing a second thermoelastic expansion in a second analyte that absorbs the second wavelength but not the first wavelength, the first and second beams extending across the entire cross sectional area of the sample wherein no portion of the sample escapes illumination by the beam as it flows through the test chamber.

6. A system as defined by claim 1, wherein said electromagnetic energy source is configured to direct a first energy beam having a first wavelength but not a second wavelength, and at a different time to direct a second energy beam having the second wavelength but not the first wavelength into the test chamber, the first energy beam inducing a first thermoelastic expansion in a first analyte that absorbs the first wavelength but not the second wavelength, the second beam inducing a second thermoelastic expansion in a second analyte that absorbs the second wavelength but not the first wavelength.

7. A system as defined by claim 1, wherein the diaphragm is arranged between a pair of electrodes, a first of the pair of electrodes within the test chamber in fluid contact with the bodily fluid sample and separated by a distance from said diaphragm, the second of the pair of electrodes external to the test chamber and separated by a distance from said diaphragm.

8. A system as defined by claim 1, wherein the diaphragm is comprised of a polymer film having a diameter between about 5 and 10 mm.

9. A system as defined by claim 1, wherein the diaphragm is comprised of PVDF film.

10. A system as defined by claim 1, wherein the diaphragm is comprised of PVDF film with a thin layer of metal on at least one surface.

11. A system as defined by claim 1, wherein the diaphragm comprises a metal plated polymer film.

12. A system as defined by claim 1, wherein:
said test chamber includes a first pair of opposing sidewalls having a first width and a second pair of opposing sidewalls having a second width that is greater than the first; and,
said energy source is directed through said first pair of opposing sidewalls and said diaphragm arranged on one of said second pair of sidewalls.

13. A system for detecting one or more analytes in a bodily fluid comprising:
a test chamber having at least one sidewall and configured to contain at least a portion of a bodily fluid sample;
an electromagnetic energy source configured to direct a first energy beam having a first wavelength but not a second wavelength, and at a different time to direct a second energy beam having the second wavelength but not the first wavelength into the test chamber, the first energy beam inducing a first thermoelastic expansion in a first analyte that absorbs the first wavelength but not the second wavelength, the second beam inducing a second thermoelastic expansion in a second analyte that absorbs the second wavelength but not the first wavelength; and,
a sensor configured to detect both of said first and said second thermoelastic expansion in said bodily fluid sample in said test chamber.

14. A system as defined by claim 13 wherein said electromagnetic energy source comprises a laser pulsing at a frequency faster than a millisecond.

15. A system as defined by claim 13 and further comprising:
a reservoir, a conduit, and a pump, said reservoir communicating with said test chamber via said conduit, said pump arranged along said conduit to urge said sample from said reservoir to said test chamber;
wherein said electromagnetic energy source comprises a pulsed laser; and,
wherein said test chamber at least one sidewall comprises at least a first and a second sidewall, said first sidewall being narrower than said second sidewall, said pulsed laser directed through said first sidewall and said sensor arranged on said second sidewall.

16. A system as defined by claim 13 and wherein said test chamber is transparent and wherein said electromagnetic energy source comprises a pulsed laser having a beam that illuminates an entire cross section of said test sample as it passes through said test chamber.

17. A system as defined by claim 13, wherein:
said test chamber includes a first pair of opposing sidewalls having a first width and a second pair of opposing sidewalls having a second width that is greater than the first; and, said energy source is directed through said first pair of opposing sidewalls and said sensor arranged on one of said second pair of sidewalls.

18. A system for detecting one or more analytes in a bodily fluid comprising:
- a test chamber having at least a first and a second sidewall and configured to contain at least a portion of a bodily fluid sample, said first sidewall narrower than said second sidewall;
- a reservoir, a conduit, and a pump, said reservoir communicating with said test chamber via said conduit, said pump arranged along said conduit to urge said sample from said reservoir to said test chamber;
- a pulsed laser configured to direct a beam into said test chamber through said first sidewall and to induce a thermoelastic expansion in said one or more analytes; and,
- a sensor configured to detect said thermoelastic expansion in said bodily fluid sample in said test chamber, said sensor comprising an acoustic sensor having a diaphragm that is deflected when an acoustic wave generated by said thermoelastic expansion strikes it, said acoustic sensor arranged on said test chamber second sidewall.

19. A system as defined by claim 18 wherein said acoustic sensor diaphragm comprises a piezoelectric diaphragm in fluid contact with said test sample, wherein said acoustic sensor further comprises first and second electrodes arranged about opposing sides of said piezoelectric diaphragm.

20. A system as defined by claim 18, wherein a first side of said diaphragm is in fluid contact with the bodily fluid sample and an opposing second side is exposed to the environment.

* * * * *